(12) United States Patent
Wulff et al.

(10) Patent No.: US 11,918,283 B2
(45) Date of Patent: Mar. 5, 2024

(54) NEUTRAL ELECTRODE AND METHOD FOR THE FORMATION THEREOF

(71) Applicant: Erbe Elektromedizin GmbH, Tuebingen (DE)

(72) Inventors: Erik Wulff, Gomaringen (DE); Marcus Felstead, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 303 days.

(21) Appl. No.: 17/146,690

(22) Filed: Jan. 12, 2021

(65) Prior Publication Data
US 2021/0212762 A1 Jul. 15, 2021

(30) Foreign Application Priority Data

Jan. 13, 2020 (EP) ..................................... 20151509

(51) Int. Cl.
*A61B 18/16* (2006.01)
*A61B 17/00* (2006.01)
*A61B 18/00* (2006.01)

(52) U.S. Cl.
CPC ...... *A61B 18/16* (2013.01); *A61B 2017/00526* (2013.01); *A61B 2018/00178* (2013.01);
(Continued)

(58) Field of Classification Search
CPC .......... A61B 18/16; A61B 2018/00178; A61B 2018/00273; A61B 2018/00791; A61B 2018/167; A61B 2017/00526; A61N 1/0496; A61N 1/14; H01B 1/06; H01B 1/22; H01B 1/24
See application file for complete search history.

(56) References Cited

U.S. PATENT DOCUMENTS 6,148,233 A * 11/2000 Owen .................. A61N 1/0476
607/5
6,208,902 B1 3/2001 Boveja
(Continued)

FOREIGN PATENT DOCUMENTS

DE 9101366 U1 6/1991
DE 4232255 C1 2/1994
(Continued)

OTHER PUBLICATIONS

Extended European Search Report dated Jul. 22, 2020, in corresponding European Application No. 20151509.5, with machine English translation (21 pages).
(Continued)

*Primary Examiner* — Khadijeh A Vahdat
(74) *Attorney, Agent, or Firm* — Fitch, Even, Tabin & Flannery LLP

(57) ABSTRACT

A neutral electrode (12) is formed on the patient (11) in that an electrically conductible mass that can solidify is applied on the skin of the patient (11). An electrically conductible inlay (17) can be arranged on or embedded in the forming electrode body (16) prior, during or after the application of the mass, the inlay (17) is or can be connected with the neutral electrode connection cable (13). The inlay (17) serves to electrically contact the electrode body (16) in a large area that in turn establishes a reliable electrical contact to the patient (11).

13 Claims, 3 Drawing Sheets

(52) U.S. Cl.
CPC .............. *A61B 2018/00273* (2013.01); *A61B 2018/00791* (2013.01); *A61B 2018/167* (2013.01)

(56) References Cited

U.S. PATENT DOCUMENTS

| | | | |
|---|---|---|---|
| 6,526,303 B1 * | 2/2003 | Scampini | A61N 1/0492 600/386 |
| 7,426,415 B2 | 9/2008 | Kühner | |
| 2003/0134545 A1 | 7/2003 | McAdams et al. | |
| 2007/0049914 A1 * | 3/2007 | Eggleston | A61B 18/16 606/32 |
| 2008/0161746 A1 | 7/2008 | Visco et al. | |
| 2008/0281310 A1 | 11/2008 | Dunning et al. | |
| 2013/0158543 A1 | 6/2013 | Dunning et al. | |
| 2019/0357847 A1 * | 11/2019 | Franke | A61L 31/145 |

FOREIGN PATENT DOCUMENTS

| | | |
|---|---|---|
| WO | 2004/069070 A1 | 8/2004 |
| WO | 2018/227165 A1 | 12/2018 |

OTHER PUBLICATIONS

John G. Webster, "Interference and Motion Artifact in Biopotentials", IEEE 1977 Region Six Conference Record, 1977, pp. 53-64, IEEE, Portland, Oregon, USA (12 pages).

National Intellectual Property Administration, P. R. China, Office Action in corresponding CN Patent Application No. 202110042061.4, dated Oct. 18, 2023; 23 pages.

* cited by examiner

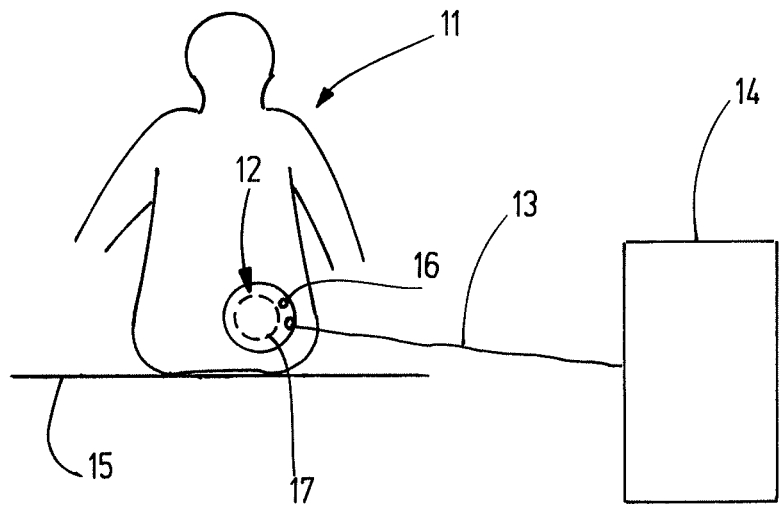
Fig.1
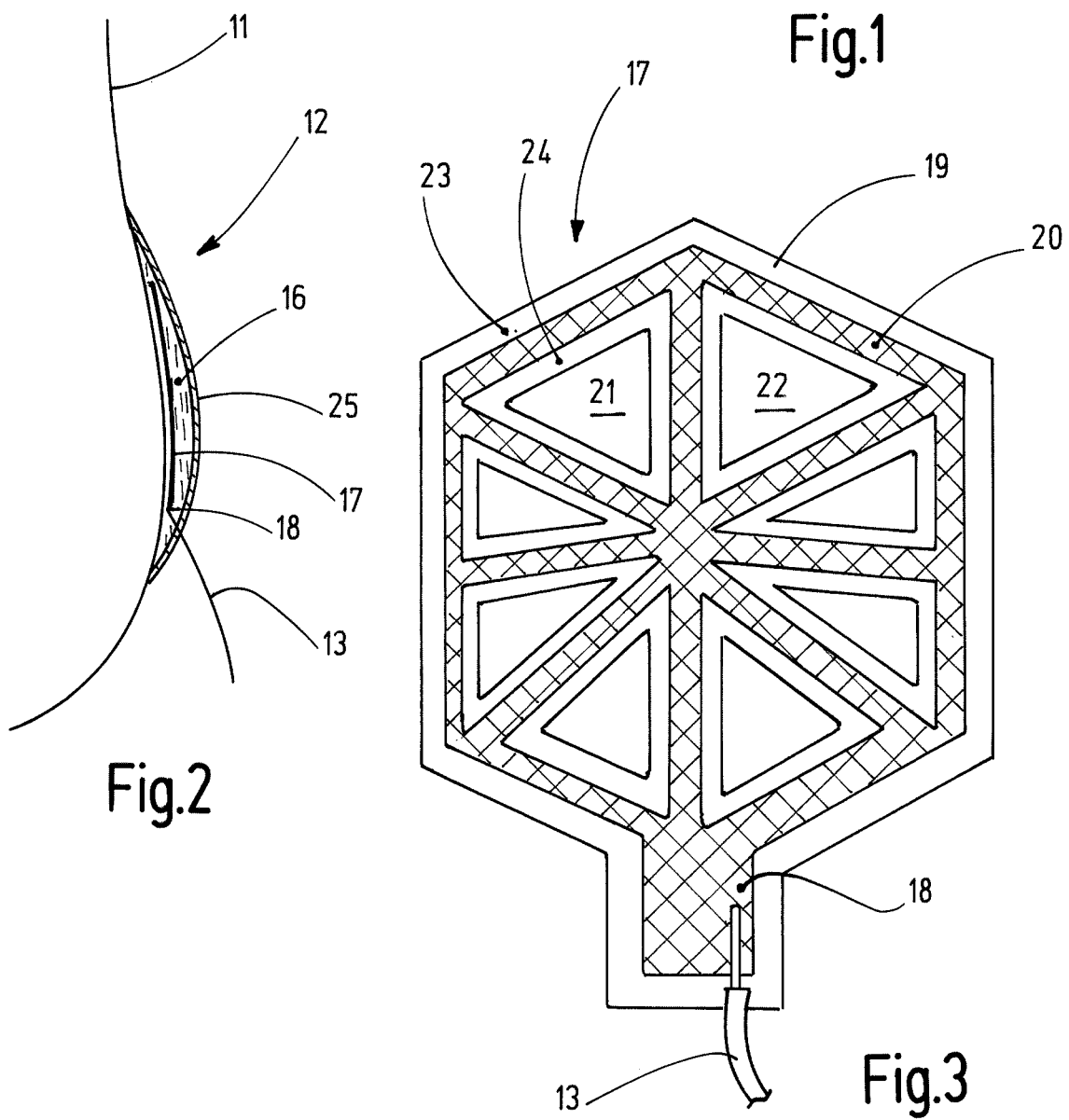
Fig.2
Fig.3

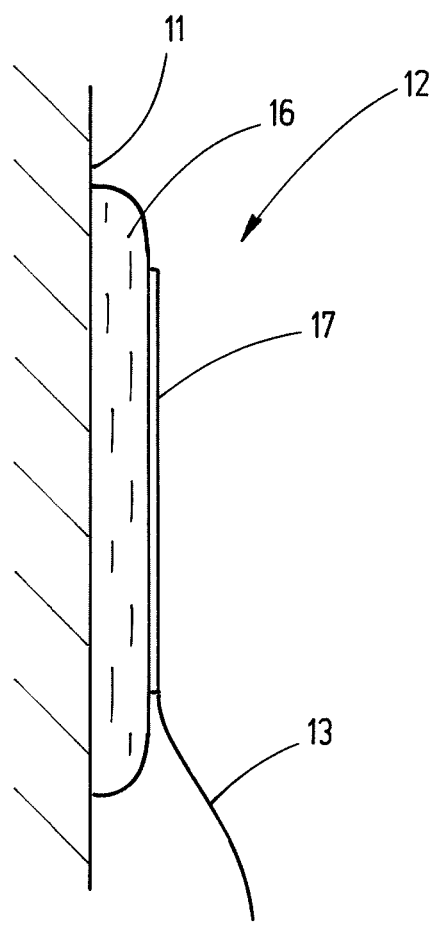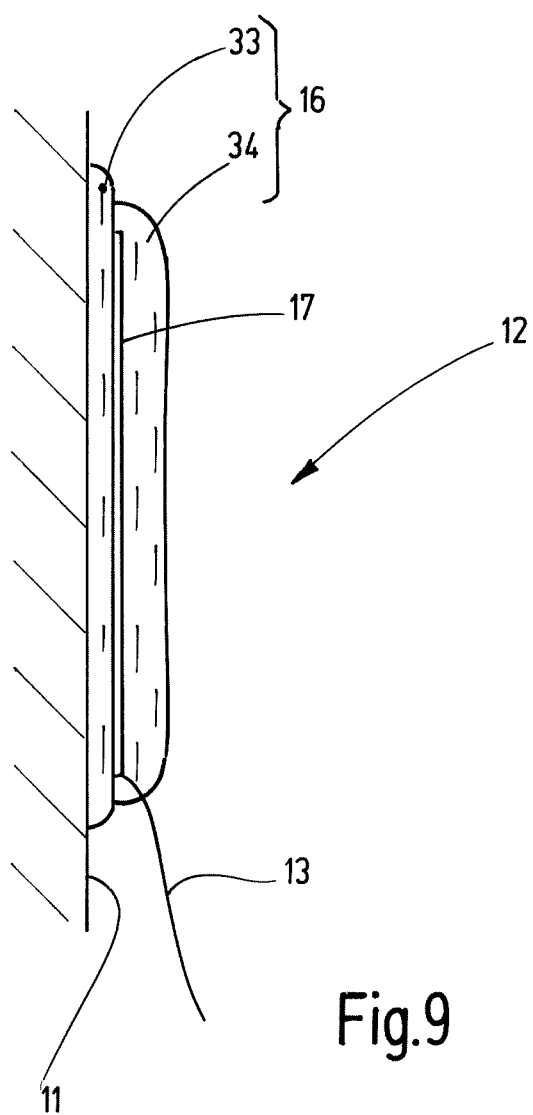

NEUTRAL ELECTRODE AND METHOD FOR THE FORMATION THEREOF

RELATED APPLICATION(S)

This application claims the benefit of European Patent Application No. 20151509.5, filed Jan. 13, 2020, the contents of which are incorporated herein by reference as if fully rewritten herein.

TECHNICAL FIELD

The invention refers to a neutral electrode for attachment on a patient for conducting of electrosurgical currents, a method for formation of such an electrode as well as a product for use during the formation of such a neutral electrode.

BACKGROUND

A neutral electrode for radio frequency surgery is known from WO 2004/069070 A1 that is configured as completely or in partial areas electrically conductible stocking.

In addition, a reusable neutral electrode is known from the utility model DE 9101366 U1 that comprises a two-dimensional support of elastic silicone rubber. It supports two electrode areas that are electrically conductible and electrically separated from each other and that are connected via connection lines with a cable. The electrode areas are connected with a neutral connection of an electrosurgical device via this cable. A monitoring system thereby checks the correct abutment of the electrode areas on the patient body.

A similar neutral electrode is known from DE 42 32 255 C1. It also comprises a two-dimensional support with multiple conductible areas that are partial electrodes of the neutral electrode. A support foil serves for attachment on the patient that comprises electrically conductible adhesive films on both sides in order to create a galvanic connection between the partial electrodes and the patient.

On one hand, neutral electrodes have to be dimensioned sufficiently large on one hand in order to keep the current density and thus the heat development on the patient below physiological limits. On the other hand, the attachment of large neutral electrodes, particularly on body regions with larger curvatures poses a problem. However, the neutral electrode has to be attached on the patient in a reliable and two-dimensional manner in order to avoid tissue damages. For monitoring a correct attachment, some neutral electrodes comprise individual partial electrodes connected to a monitoring device that inhibits the operation of an electrosurgical device as soon as a resistance limit value between two partial electrodes is exceeded.

Restrictions result from the above aspects in terms of the location of the neutral electrode on the patient, such that sometimes undesired large distances between the neutral electrode and the surgery area is present. In addition, the position of the cable connected to the neutral electrode can be obstructive.

It is one object of the invention to provide a concept for a neutral electrode with which a reliable electric contact between a neutral line and the patient can be created and that is flexible in terms of handling and attachment.

SUMMARY

The neutral electrode according to the invention comprises an electrode body made of an electrically conductible material applied to the skin of the patient in liquid, pulpy or pasty condition and solidified at least partly there. The shapeless material is not placed on the body of the patient in a solidified condition and thus is in firm contact with the skin of the patient, irrespective of potential body hair. In addition, the shape of the material applied to the patient matches with each body shape such that a complete two-dimensional attachment is to be expected in any case. In addition, by applying an appropriate amount of the shapeless material, the electrode thickness can be adapted to the respective application.

The applied material is electrically conductible and serves to conduct the electrosurgical current from the patient to a neutral electrode connection cable. Some time after the material has been applied in a non-solidified condition it has completely or partly solidified, wherein the solidification is preferably at least provided on the side of the electrode body facing away from the patient. For example, the electrode body can consist of a material that dries superficially and thus forms a skin or protection layer on the side facing away from the patient. The material can also solidify completely and in this manner form a preferably plastically or elastically remaining body or also a rigid body.

The solidification can be based on evaporation of solvents and/or on a chemical reaction, e.g. a cross-linking reaction, in that components of the material react with oxygen or other components of the air. Also humidity, e.g. of the skin of the patient originating humidity and/or air humidity, can initiate a chemical reaction process in the context of which the material of the electrode establishes cross-links, for example, or solidifies in another manner.

The electrode body comprises an inlay that comprises a cable connector surrounded by the electrode body or is at least in firm abutment therewith. This inlay is preferably an electrically conductible two-dimensional element of a material, the specific conductivity thereof is higher than that of the material of the electrode body. The inlay is, for example, a net, a knitted fabric, a woven fabric, a grid, a perforated foil, a non-perforated foil, a perforated or non-perforated plate or the like. For example, the inlay is arranged during the formation of the neutral electrode on the patient's body and is then surrounded by the not yet solidified material, after which the applied material solidifies. Thus, the neutral electrode is ready for operation. The inlay has preferably a predetermined contour and always the same size also in different applications. The size of the neutral electrode may however vary, in that the shapeless material is applied in a larger or smaller area.

The electrode body can be made of an electric conductible non-metallic material, e.g. of a substance mixture that contains a solvent at least as long as the electrode body is not completely solidified. Particularly, the material can contain water, ethanol, diethyl ether, isooctane, ethyl acetate and/or other volatile, preferably unipolar liquid compounds. Also, the material can contain a polymer, e.g. polyvinyl pyrrolidone, nitro cellulose, ethyl cellulose and/or poly(methyl acrylate isobutene-monoisopropylmaleate), cyanoacrylate, e.g. 2-optylcyanoacrylate, siloxane polymer, e.g. hexamethylene disiloxane. In addition, the material can contain sodium chloride in aqueous solution or other salts in aqueous solution and/or electron-conductible particles, such as for example carbon particles, metal particles or particles of conductible ceramic for creation or improvement of the electric conductivity. Therefore, the electrode body can consist of a gel having an evaporation component or of an electrode body having a curable component as well as an electrically conductible component. The evaporation components can be highly volatile solvents, such as for example ethyl alcohol, ether or another of the other solvents mentioned above. The solidifying components can be one or more of the above-mentioned cross-linkable substances. It is also possible to provide the material of the electrode body in two separate components that form a solidifying and/or curing mixture, if they are brought in contact with each other. Further the material can contain a gel-forming component for formation of the electrode. The gel-forming component supports the formation of the electrode body in sufficient thickness of preferably more than one, preferably multiple millimeters. The gel-forming component is particularly configured to hydrogel formation, such as for example farina, gelatine, polyacrylic acid or other suitable substances for formation of carbomers.

The inlay is preferably a metal structure in the form of foils, wires, nets or a two-dimensional body having multiple through-holes, such as a multiply perforated metal foil. The inlay can also be a metallized plastic, metallized paper or another body provided with a conductible coating or a metal foil provided with an insulation on one side. It is particularly possible to configure the inlay electrically insulating on the side of the patient in order to avoid direct local contact between the highly conductible metal of the inlay and the patient. However, the inlay is in electric galvanic contact with the potentially slightly less conductible material of the electrode body, such that current that has to be conducted by the inlay is transmitted from the patient via the electrode body.

If the inlay is isolated on one side, it is possible that the area covered by the electric conductible region on the non-metallic non-electrically conductible support is smaller than that of the support. In doing so, the electrically insulating support extends beyond the conductible regions and keeps them away from the skin of the patient. This measure avoids local current concentrations on the skin of the patient along the edges of the electric conductible regions.

The cable connector can be configured for releasable connection with a cable or can be non-releaseably connected with a cable set. In the latter case the cable forms part of a neutral electrode that is to be created on the patient and has to be disposed completely after use.

The inventive method for attachment of a neutral electrode on the patient comprises the arrangement of the inlay on the skin of the patient and the application of shapeless material that at least partly solidifies or is solidified after application. The inlay is then embedded in the electrode body. The electrode body is not sticky anymore after the at least partly solidification on the outside and at least adhesively connected in the edge region with the skin of the patient. It can be solidified or also of gel-like consistency inside. This supports the flexibility, the electric contact and simplifies the later removal of the neutral electrode from the skin of the patient.

Prior to the step of the attachment of the inlay on the patient, the shapeless material or a portion thereof can already be applied on the skin of the patient, such that the inlay sticks to the skin surface. If the applied layer of the shapeless material that can be solidified is sufficiently thick in order to distribute the current originating from the inlay, the inlay can be attached to the material just like to a thickly applied adhesive. The application of additional material can be omitted. Then a neutral electrode is formed, the metal inlay of which is arranged at the outer side of the electrode. The advantage of this method is the outward covering of the not yet solidified electrode body.

The neutral electrode according to the invention is preferably created under use of a product that is only provided for creation of the neutral electrode on a patient. The product comprises a shapeless mass provided in a container, wherein the mass is electrically conductible and can be solidified. The mass forms the material of which the electrode body consists after application on the skin of the patient. The mass is preferably liquid, pulpy or pasty and extrinsically or intrinsically electrically conductible. For example, it can contain electrically conductible particles and/or dissociated salts, e.g. NaCl in aqueous solution. An application device is preferably part of the container, e.g. in the form of a spray head, a dispenser with a pump, similar to a soap dispenser, a cover provided with a brush or a spatula, brush, roller or the like added to the container. In addition, the product can be part of a set comprising in addition to the mentioned container one or more inlays and, if necessary, one or more neutral electrode connection cables.

Different sizes of neutral electrodes can be realized due to using different amounts of the, e.g. gel-like shapeless mass. The used amount is based on the planned application or power of the electrosurgical generator. Thereby the generator can be configured to define requirements for the amount of the gel or the necessary size of the neutral electrode depending on user adjustments (mode, effect level, etc.).

BRIEF DESCRIPTION OF THE DRAWINGS

Further details of advantageous embodiments of the invention are apparent from the dependent claims, from the drawings or the description. The drawings show:

FIG. 1 a patient with neutral electrode attached thereon in schematic illustration, FIG. 2 the patient with attached neutral electrode in a partly sectional illustration, FIG. 3 an inlay that is part of the neutral electrode according to FIG. 2 in a schematic top view, FIG. 4 the neutral electrode according to FIG. 2 in enlarged schematic sectional illustration, FIG. 5 a further enlarged partly sectional illustration of the neutral electrode according to FIG. 4, FIG. 6 a still further enlarged partly illustration of a part of the electrode body with electrically conductible particles, FIG. 7 a container configured as spray bottle with a mass contained therein for formation of the neutral electrode in a vertical sectional illustration, FIG. 8 a container with a mass contained therein and a cover brush in a vertical sectional illustration, FIG. 9 a modified embodiment of an inventive neutral electrode in a longitudinal sectional illustration, FIG. 10 a yet further modified embodiment of a neutral electrode in a schematic longitudinal sectional illustration.

DETAILED DESCRIPTION

Figure 4:
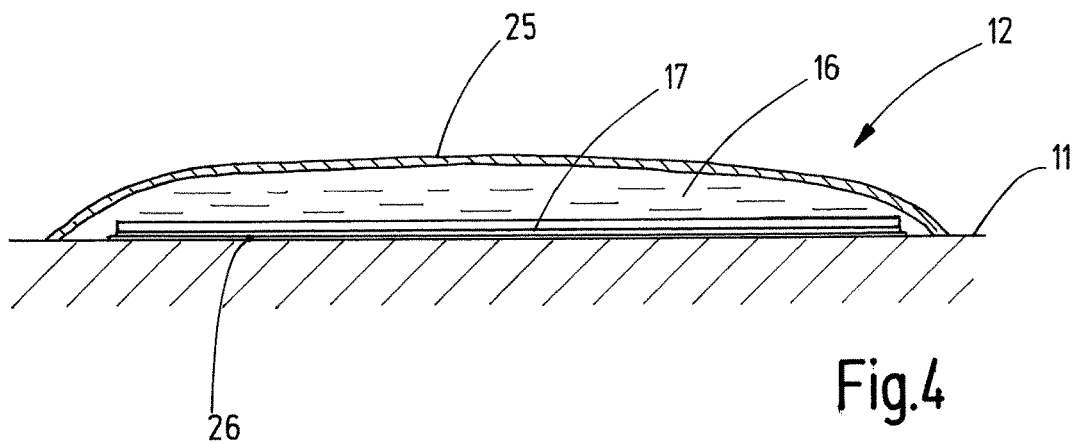

FIG. 1 illustrates a neutral electrode 12 attached to a patient 11 that is connected with an apparatus 14 via a neutral electrode connection cable 13, wherein the apparatus 14 serves, e.g. for electrosurgery. The attachment of the neutral electrode 12 on the patient 11 can be carried out, for example, during the preparation of the patient 11 for surgery while the patient sits or lies on a base 15. The location of the neutral electrode 12 can be based on medical or surgery technical considerations. No specific consideration has to be shown for body curvatures, folds or the like.

FIG. 2 illustrates the neutral electrode 12 on a curved skin portion of the patient 11. The neutral electrode 12 consists of an electrode body 16 and an inlay 17 embedded therein. The latter is electrically connected with the neutral electrode connection cable 13 at a cable connector 18 that is also apparent in FIG. 3. The cable connector 18 can be formed by a rigid electrically conductible connection of the conductor of the neutral electrode connection cable 13 with the inlay 17 or by a releasable connection, such as for example a snap fastener, a clamp or the like.

The inlay is an at partly electrically conductible element that preferably surrounds at least one area that is so large that the current that has to be conducted by the neutral electrode connection cable 13 divided through the area circumscribed by the inlay is below a physiological current density limit value. In the simplest case the inlay 17 can be a section of the conductor of the neutral electrode connection cable 13 stripped from the insulation and bent into a ring or another suitable form. However, it can also be an individual element of metal or another electrically conductible material, such as for example conductible rubber, that extends over an area. The area can have, e.g. the size of the palm of the hand.

In the present embodiment the inlay 17 has a substantially hexagonal circumference and consists of an electric non-conductible support 19, e.g. of plastic foil, paper or the like. On this support 19 is attached, preferably on the side facing away from the patient that is galvanically connected with the cable connector 18. Preferably the cable connector 18 and the conductor 20 are formed by a thin continuous metal layer that consists, e.g. of strip-shaped sections that together form a net. The strip-shaped sections extend preferably around at least one opening 21 as well as, if necessary, around multiple openings that are formed in the support 19. Thereby the strip-shaped conductor sections are preferably narrower than the respective sections of the support 19 such that outward around the conductor as well as around each opening 21, 22 distance areas 23, 24 are defined.

The carrier 19 can be provided with an electrically non-conductible or also with an electrically conductible adhesive layer on the side facing the patient 11. The specific conductivity of this adhesive layer is preferably less than the specific conductivity of metal, further preferably however higher than the specific electric conductivity of the electrode body. This measure ensures a uniform current density distribution below the neutral electrode 12.

The electrode body 16 formed on the patient 11 for the formation of the neutral electrode 12 covers the inlay 17 and sticks to the skin of the patient 11. The neutral electrode 12 is in contact with the skin of the patient 11 in a region surrounding the inlay 17. In addition, the electrode body 16 extends through the openings 21, 22 and is also there in contact with the skin of the patient 11.

The electrode body 16 consists preferably of an electrically conductible material that can solidify in the air that at least forms solidified non-sticky layer or skin 25 on the side facing away from the patient 11. Below this layer 25 the material of the electrode body 16 can also be solidified or also can be less solidified or non-solidified. FIG. 4 schematically illustrates this configuration at the beginning of the solidification of the electrode body 16. The layer 25 sticks at its edge to the skin of the patient. It can be a layer that has solidified by drying, i.e. evaporation of a solvent or by cross-linking of a polymer. For example, the electrode body 16 can contain amongst others an alcoholic acrylate copolymer/polyurethane solution that can in addition contain dimethyl ether. By volatilization of the contained ethanol and/or the dimethyl ether, the electrode body 16 solidifies from the outside to the inside, wherein the solidified zone can extend up to the inlay 17 and, if applicable, also up to the skin of the patient 11. Non-solidified regions can remain, which simplifies the later release of the neutral electrode after use.

The inlay 17 may have been attached to the skin of the patient by means of an adhesive layer 26 as mentioned. It is, however, also possible to omit a separate attachment of the inlay 17 on the skin of the patient 11. This is particularly advisable, if the inlay consists of only narrow strips or wires, e.g. in the shape of a woven fabric, net or knitted fabric.

Figure 5:
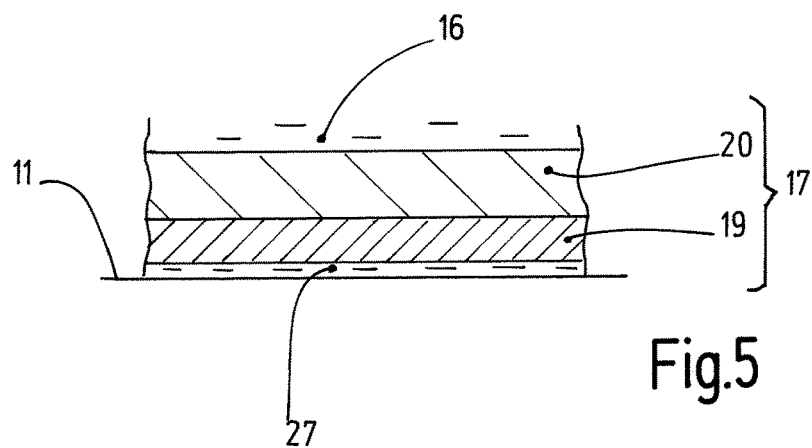

It is also possible to use the material of the electrode body 16 itself for attachment of the inlay 17. For this FIG. 5 illustrates a section of the neutral electrode 12 in enlarged sectional view. Here the electrode body 16 extends through the inlay 17 and forms a thin layer-like zone 27 below the electrode body 16 and between the inlay 17 and the patient 11 that is electrically conductible and sticks in a two-dimensional manner to the patient 11. This embodiment allows an improved current distribution compared with the embodiment according to FIG. 4, if the latter uses an electrically non-conductible adhesive 26 or operates with an inlay 17 without direct attachment to the skin of the patient 11.

Figure 6:
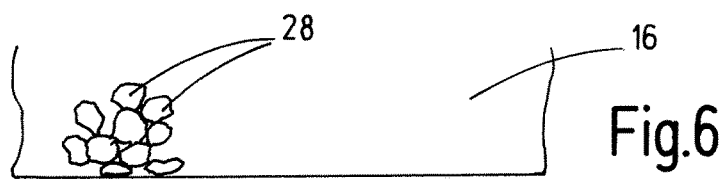

The material of the electrode body 16 can be intrinsically conductible in that it contains, e.g. sodium chloride in an aqueous solution, acetic acid or other substances that can conduct ions such as aqueous soap solution or the like. The material of the electrode body 16 can be, however, also extrinsically conductible, as illustrated in FIG. 6 in highly enlarged manner. The material of the electrode body 16 forms a matrix that is filled with electrically conductible particles 28, e.g. metal particles, particles of conductible ceramic, carbon black, graphite powder or the like. The material of the electrode body 16 can also be characterized by a combination of the compounds mentioned above. For example, a mixture of ion conductible material and conductible particles can be provided. Thus, the material can be extrinsically as well as intrinsically conductible. So a high specific conductivity can be reached that is particularly higher than the specific conductivity of the skin. In doing so, the neutral electrode 12 forms an equipotential area.

Figures 7, 8:
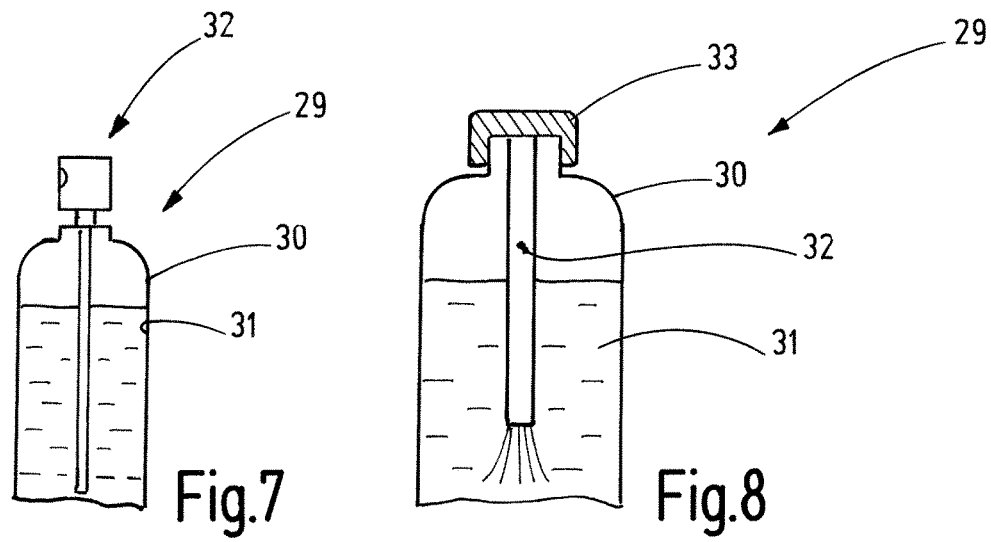

FIG. 7 illustrates a package 29 that can form a set together with the inlay 17 according to FIG. 3. The package 29 comprises a container 30 configured as spray bottle or dispenser containing a shapeless and preferably liquid mass 31. The mass 31 is, for example, an alcoholic acrylate copolymer/polyurethane solution. The container 30 closed to the outside is provided with an application device 32, e.g. in the form of a spray head. If the container 30 is filled with a pressure gas or another blowing agent, the application device 32 comprises a valve and an atomizing device. If the container 30 is however pressureless, the application device 32 comprises a pump device and a dispenser device. It can be configured as simple round nozzle, slit nozzle, quench head or atomizing device.

The shapeless mass 31 can also be of a pulpier consistence. For this FIG. 8 illustrates a container 30 having a cap 33 on which a brush is attached serving as application device 32. The mass 31 contained herein can contain components in addition to the mentioned components that define the consistency, particularly swellable components, such as farina, gel former or the like in order to allow an application of the shapeless mass on the skin of the patient in a layer as thick as possible, such that the forming electrode body is not only provided as thin film, but as rind-like skin.

The formation of the neutral electrode on the patient 11 can occur as follows:

If the inlay 17 is provided with an electrically conductible or also an electrically insulating adhesive on at least one side, the inlay 17 is first attached to the skin of the patient 11 after which the mass 31 of the package 29 according to FIG. 7 or 8 is applied on the inlay 17 and covering it thereby. After at least superficial solidification of the applied mass, the neutral electrode 12 is ready for operation.

In a second variation that is already suggested by FIG. 5 and that is particularly suitable, if the inlay 17 does not comprise an adhesive layer on the side of the patient, first a thin layer of the shapeless mass is applied on the skin of the patient. After that the inlay 17 is placed on top (FIG. 5) and shapeless mass is further applied in the following until the electrode body 16 is provided in the desired layer thickness.

For inlays 17 without insulation on the patient side the variations according to FIGS. 9 and 10 are particularly appropriate. For example, for this first a first layer 33 of the electrode body 16 is arranged on the skin of the patient 11 according to FIG. 9 and before drying or another solidification thereof the inlay 17 is attached. It is then covered by a second layer 34 of the material of the electrode body 16 such that it finally encloses the inlay 17.

It is in addition also possible to apply the electrode body 16 in a first step on the skin of the patient 11 according to FIG. 10 and to attach the inlay 17 then on the outside of the still sticky electrode body 16. A neutral electrode is formed having an inlay located on the outside.

It is common to all of the above-mentioned embodiments and variations that the neutral electrode 12 can be provided in addition with a temperature sensor or other sensors for monitoring the current density, the temperature or other physical parameters. Such sensors can be attached on the inlay 17 or can be embedded separately in the electrode body 16.

Sets can be provided that comprise one or more packages 29 and one or more inlays 17. The number of inlays 17 can be larger than the numbers of packages 29. Also the inlays 17 can be provided in different shapes or sizes in order to match with different applications. In addition, a stencil can form part of the set that can border the outer edge of the application region during spraying or brushing or otherwise applying the mass 31 and can thus define the contour of the neutral electrode 12. One or more sensors, e.g. temperature sensors can be part of the set.

An inventive neutral electrode 12 is formed on the patient 11 in that an electrically conductible mass that can solidify is applied on the skin of the patient 11 that is electrically conductible. An electrically conductible inlay 17 can be arranged on or embedded in the forming electrode body 16 prior, during or after the application of the mass, the inlay 17 is or can be connected with the neutral electrode connection cable 13. The inlay 17 serves to electrically contact the electrode body 16 in a large area that in turn establishes a reliable electrical contact to the patient 11.

If a neutral electrode monitoring is desired in this manner, also two neutral electrodes can be attached to the skin of the patient 11 with distance from one another that are separately connected with respective neutral electrode connectors or a combined connector of a monitoring apparatus 14 respectively. It can use both electrodes on the same level for current conduction away from the patient and can check the correct function and contacting on the patient by resistance monitoring between the electrodes.

LIST OF REFERENCE SIGNS

11 patient
12 neutral electrode
13 neutral electrode connection cable
14 apparatus
15 base
16 electrode body
17 inlay
18 cable connector
19 support
20 conductor
21, 22 openings
23, 24 distance areas
25 layer
26 adhesive
27 zone
28 particle
29 package
30 container
31 mass
32 application device
33, 34 layers

The invention claimed is:

1. A method for attaching a neutral electrode on a patient (11) for conducting of electrosurgical currents, the method comprising:
    forming the neutral electrode on an exterior surface of a skin of the patient (11) by:
    attaching an electrically conductive inlay (17) to the exterior surface of the skin of the patient;
    applying a shapeless mass (31) on the exterior surface of the skin of the patient and onto a surface of the electrically conductive inlay (17) facing away from the exterior surface of the skin of the patient and allowing the shapeless mass to solidify at least partly thereon;
    wherein the shapeless mass is electrically conductive and the electrically conductive inlay (17) is configured to be connected via an electrically conductive connector or cable to an electrosurgical generator.

2. The method of claim 1, wherein the electrically conductive inlay is a metal inlay and comprises a cable connector (18).

3. The method of claim 2, wherein the cable connector (18) is either configured for releasable connection with the cable (13) or is unreleaseably connected with the cable (13).

4. The method of claim 1, wherein the shapeless mass (31) is of an electrically conductive and non-metallic material.

5. The method of claim 1, wherein the shapeless mass (31) comprises a gel having an evaporable component.

6. The method of claim 1, wherein the shapeless mass (31) comprises a curing component.

7. The method of claim 1, wherein the shapeless mass (31) comprises an air-curable component.

8. The method of claim 1, wherein the shapeless mass (31) comprises an ion conductible material.

9. The method of claim 1, wherein the shapeless mass (31) comprises particles (28) that are configured to conduct electrons.

10. The method of claim 1, wherein attaching an electrically conductive inlay (17) to the exterior surface of the skin comprises placing an insulated side of a metal inlay on the exterior surface of the skin of the patient.

11. The method of claim 1, wherein the electrically conductive inlay is a metal inlay (17) and the metal inlay (17) is connected with a temperature sensor or another sensor.

12. The method of claim 1, wherein attaching the electrically conductive inlay (17) to the exterior surface of the skin of the patient comprises applying the electrically conductive inlay (17) such that at least a portion of the shapeless mass is present between the skin of the patient and the inlay.

13. The method of claim 1, wherein the electrically conductive inlay (17) is sized such that a current density resulting from an applied electrosurgical current of the electrosurgical currents conducted by the electrically conductive inlay (17) is below a value at which tissue damage occurs.

\* \* \* \* \*